United States Patent [19]

Kay et al.

[11] 4,350,892

[45] Sep. 21, 1982

[54] X'-, Y'-, Z'- AXIS MULTIDIMENSIONAL SLIT-SCAN FLOW SYSTEM

[75] Inventors: David B. Kay, Rochester; Leon L. Wheeless, Jr., Webster, both of N.Y.

[73] Assignee: Research Corporation, New York, N.Y.

[21] Appl. No.: 174,280

[22] Filed: Jul. 31, 1980

[51] Int. Cl.$^3$ .............................................. G01N 21/64
[52] U.S. Cl. ................................... 250/461.2; 356/318
[58] Field of Search ............... 250/461 B; 356/39, 318

[56] References Cited

U.S. PATENT DOCUMENTS

| | | | |
|---|---|---|---|
| Re. 29,141 | 2/1977 | Hogg | 356/36 |
| 2,656,508 | 10/1953 | Coulter | 324/71 CP |
| 3,327,117 | 6/1967 | Kamentsky | 250/461 R |
| 3,327,119 | 6/1967 | Kamentsky | 250/461 R |
| 3,470,373 | 9/1969 | Brewer et al. | 250/461 R |
| 3,497,690 | 2/1970 | Wheeless, Jr. et al. | 250/461 R |
| 3,657,537 | 4/1972 | Wheeless, Jr. | et al./250 |
| 3,699,336 | 10/1972 | Ehrlich et al. | 250/461 R |
| 3,705,771 | 12/1972 | Friedman et al. | 356/39 |
| 3,710,933 | 1/1973 | Fulwyler et al. | 209/3.1 |
| 3,785,735 | 1/1974 | Friedman et al. | 356/39 |
| 3,788,744 | 1/1974 | Friedman et al. | 356/39 |
| 3,883,247 | 5/1975 | Adams | 356/39 |
| 3,918,812 | 11/1975 | Holm | 356/73 |
| 3,960,449 | 1/1976 | Carleton et al. | 356/340 |
| 4,031,399 | 6/1977 | Klein et al. | 250/461 B |

OTHER PUBLICATIONS

Kay, D. B. et al., "Experimental Findings on Gynecologic Cell Orientation and Dynamics for Three Flow Nozzle Geoometries", *J. Histochem. Cytochem.*, vol. 25, No. 7, pp. 870–874, (1977).

Fulwyler, M. J., "Hydrodynamic Orientation of Cells", *J. Hostochem. Cytochem.*, vol. 25, No. 7, pp. 781–783, (1970).

Wheeless, L. L. et al., "Slit-Scan Cytofluorometry: Basis for an Automated Cytopathology Prescreening System", *Acta. Cytol.*, vol. 17, No. 5, pp. 391–394, (1973).

Wheeless, L. L. et al., "Slit-Scan Cytofluorometry: Data Base for Automated Cytopathology", *Acta. Cytol.*, vol. 19, No. 5, pp. 460–464, (1975).

Cambier, M. S. et al., "Slit-Scan Cytofluorometry Basis for Automated Prescreening of Urinary Tract Cytology", *J. Histochem. Cytochem.*, vol. 24, No. 1, pp. 305–307, (1976).

Cambier, J. L. et al., "The Binucleate Cell: Implications for Automated Cytopathology", *Acta. Cytol.*, vol. 19, No. 3, pp. 281–285, (1975).

Wheeless, L. L. et al., "Slit-Scan Cytofluorometry", *Acta. Cytol.*, vol. 17, No. 4, pp. 333–339, (1973).

Wheeless, L. L. et al., "Slit-Scan Flow System for Automated Cytopathology", *Acta. Cytol.*, vol. 19, No. 1, pp. 45–52, (1975).

Wheeless, L. L. et al., "Imaging Systems for Correlation of False Alarms in Flow", *J. Histochem. Cytochem.*, vol. 25, No. 7, pp. 864–869, (1977).

Kay, D. B. et al., "Imaging System for Correlating Fluorescence Cell Measurements in Flow", *Clever Optics*, vol. 126, pp. 132–139, (Aug. 25–26, 1977).

Cambier, J. L. et al., "A Multi-Dimensional Slit-Scan Flow System", *J. Histochem. Cytochem.*, vol. 27, No. 1, pp. 321–324, (1979).

Kay, D. B. et al., "Imaging in Flow", *J. Histochem. Cytochem.*, vol. 27, No. 1, pp. 329–334, (1979).

Cambier, J. L. et al., "Predicted Performance of Single vs. Multiple-Slit Flow Systems", *J. Histochem. Cytochem.*, vol. 27, No. 1, pp. 335–341, (1979).

Wheeless, L. L. et al., "False Alarms in a Slit-Scan Flow System: Causes and Occurrence Rates Implications & Potential Solutions", *J. Histochem. Cytochem.*, vol. 27, No. 1, pp. 596–599, (1979).

*Primary Examiner*—Alfred E. Smith
*Assistant Examiner*—Janice A. Howell
*Attorney, Agent, or Firm*—Kerkam, Stowell, Kondracki & Clarke

[57] ABSTRACT

A cytofluorometer for simultaneously obtaining multi-dimensional slit-scan type fluorescence contours of particles, particularly biological cells, in flow. It is recognized that a cell may be effectively partitioned into orthogonal substantially planar cross sections by means of optical imaging through three slit-imaging optical systems, with each of the optical imaging systems viewing the illuminated central region of the cell. Significantly, all optical axes lie substantially in a plane perpendicular to the flow axis. As a result, the depth of focus required is only that necessary to image directly across the flow stream, rather than obliquely as in previous apparatus. This narrower depth of focus can be directly traded for a desirable increase in system resolution. Further, a two-stage flow cytofluorometer for sequentially obtaining a one-dimensional slit-scan type fluorescence contour and multidimensional slit-scan type fluorescence contours includes an optical system wherein a microscope objective lens is shared to, in addition, generate a one-dimensional slit-scan type fluorescence contour along the Z or flow axis by collecting fluorescence from a slit-illuminated region.

15 Claims, 10 Drawing Figures

X'-, Y'-, Z'- AXIS MULTIDIMENSIONAL SLIT-SCAN FLOW SYSTEM

CONTRACT CLAUSE

Support for this invention was received through National Cancer Institute Contract No. N01-CB-33862.

BACKGROUND OF THE INVENTION

The present invention relates generally to an automated cytopathology screening instrument and, more particularly, to a flow cytofluorometer for simultaneously obtaining multidimensional slit-scan type flourescence contours of particles, particularly biological cells, in flow. Various aspects of this invention are an improvement of the invention to which commonly-assigned application Ser. No. 030,880, filed Apr. 17, 1979, by David B. Kay, Leon L. Wheeless, Jr. and James L. Cambier, and entitled "MULTIDIMENSIONAL SLIT-SCAN FLOW SYSTEM" is directed, now U.S. Pat. No. 4,293,221. The entire disclosure of said application U.S. Pat. No. 4,293,221 is hereby expressly incorporated by reference.

A number of approaches have been developed directed to the problem of automating the process of analyzing cells from biological specimens. One particular, but not limiting, purpose is automated prescreening for gynecologic cancer and its precursors. Conditions for a successful system are: (1) a low specimen false negative rate; and (2) an acceptable specimen false positive rate. Achievement of these conditions requires a low single-cell false alarm rate. These functional considerations should preferably be satisfied in a cellular screening system which has a high cell throughput, and which minimizes the amount of complex computation in the analysis required. This basically translates to a question of system resolution.

At one end of the resolution scale are high-resolution systems, for example utilizing a sub-micron scanning spot, wherein a full two-dimensional image of each cell is acquired and processed by a computer. This can involve relatively long data processing and computation times, and consequent low throughput. Particular examples of high-resolution systems are disclosed in the Ehrlich et al. U.S. Pat. No. 3,699,336 and in the Holm U.S. Pat. No. 3,918,812.

At the other end of the resolution scale are low-resolution systems wherein excitation and measuring apertures are larger than the cell of interest and a gross characteristic of each cell is examined, for example total fluorescence at a particular wave-length or light scatter at a particular angle. These systems permit measurements to be made at rates up to several thousand cells per second, and provide valuable information on specific cellular substances and parameter profiles on large populations of cells. However, they have thus far failed to demonstrate a capability to provide sufficient cellular information for the decisions required for application as a screening instrument.

A number of approaches have been proposed for low-resolution systems. The Coulter U.S. Pat. No. 2,656,508 describes the Coulter sensing principle which provides an indication of cell size. Of particular interest with respect to the present invention are the low-resolution systems of the following U.S. patents, which systems generally optically view biological cells from two orientations or simultaneously examine a plurality of optical characteristics: Friedman et al. U.S. Pat. Nos. 3,705,771, 3,785,735, and 3,788,744; and Fulwyler et al. U.S. Pat. No. 3,710,933. As a particular example, the low-resolution system disclosed in the '933 Fulwyler et al patent includes a flow chamber through which cells in suspension flow sequentially in a stream, and a light beam which intersects the cell stream at right angles. The Fulwyler et al. system measures small angle light scatter in one direction, and cellular fluorescence in another.

One particularly promising medium-resolution measurement technique suitable for use in the field of automated cytology is a slit-scan technique invented by L. L. Wheeless, Jr., and S. F. Patten, Jr. This technique is initially described in the Wheeless, Jr., et al. U.S. Pat. No. 3,657,537; and in the literature reference: L. L. Wheeless, Jr., and S. F. Patten, Jr., "Slit-Scan Cytofluorometry", *Acta Cytol.*, Vol. 17, No. 4, pp. 333–339 (1973). Both static cell and flow cytofluorometers are described.

The slit-scan technique is further described, with additional details concerning flow cytofluorometers in particular, in the following representative literature references: L. L. Wheeless, Jr., J. A. Hardy and N. Balasubramanian, "Slit-Scan Flow System for Automated Cytopathology", *Acta Cytol.*, Vol. 19, No. 1, pp. 45–52 (1975); L. L. Wheeless, Jr., D. B. Kay, M. A. Cambier, J. L. Cambier and S. F. Patten, Jr., "Imaging Systems for Correlation of False Alarms in Flow", *J. Histochem. Cytochem.*, Vol. 25, No. 7, pp. 864–869 (1977); and D. B. Kay, J. L. Cambier and L. L. Wheeless, Jr., "Imaging System for Correlating Fluorescence Cell Measurements in Flow", Proceedings of the Society of Photo-Optical Instrumentation Engineers, San Diego, Calif., *Clever Optics*, Vol 126, pp. 132–139 (Aug. 25–26, 1977). The entire disclosures of each of the references identified in this and the preceeding paragraph are hereby expressly incorporated herein by reference.

The slit-scan technique provides a more complete set of cellular parameters than is available with a low-resolution optical system, without producing the large data matrix associated with a high-resolution system. It represents a compromise solution to the problem of throughput and resolution.

In particular, the slit-scan configuration sequentially records the secondary fluorescence of an elongated portion of a cell (generally transversing the width of the cell) at discrete time intervals as that cell moves relative to a slit-producing aperture, and a sequential series of planar cell volumes are defined by the slit-producing aperture as the cell relatively moves. This type of medium-resolution slit-scan provides a graphic fluorescence contour, which in essence is a plot of the averaged fluorescence along the cell. From such contours, the fluorescence from the nuclei of the cells is readily distinguishable from cytoplasmic fluorescence.

Two general approaches to implementing this concept have been proposed, as well as a hybrid approach. In the first approach, the slit is defined by optical imaging. In particular, the entire cell, or at least a substantial volume, is illuminated by excitation light, and a slit region only of the illuminated volume is viewed, for example through an optical system having a slit field stop or aperture in an image plane, such that only the secondary fluorescence from a defined planar region reaches a detector.

In the second general approach, the slit is defined by the excitation illumination, and slit-imaging is not required. Only a planar volume of the cell is excited to fluorescence, with other cellular regions remaining dark. As typically implemented in a flow system, secondary fluorescence from a cell is recorded as the cell flows through a thin "wall" of excitation illumination.

In a hybrid approach, only a planar region is excited by a slit of excitation illumination, and only the excited planar region is viewed through a suitable slit-imaging system.

In any event, the slit-producing aperture, however defined, ideally is much smaller than the diameter of the cell of interest.

The information from such a slit-scan fluorescence contour has been shown to be quite useful in prescreening. Specifically, for each cell, such characteristics as nuclear fluorescence, nuclear diameter, cytoplasmic diameter, cytoplasmic fluorescence, and nuclear-to-cytoplasmic diameter ratio (N/C ratio) may be determined. This technique is becoming increasingly useful since a comparison data base has been developed to enable the recognition of abnormal cells. In addition to the Wheeless and Patten "Slit-Scan Cytofluorometry" article identified above, the following literature references provide background information concerning the usefulness of the slit scan technique: L. L. Wheeless, Jr., and S. F. Patten, Jr., "Slit-Scan Cytofluorometry: Basis for an Automated Cytopathology Prescreening System", *Acta Cytol.*, Vol. 17, No. 5, pp. 391-394 (1973); L. L. Wheeless, Jr., S. F. Patten Jr., and M. A. Cambier, "Slit-Scan Cytofluorometry: Data Base for Automated Cytopathology", *Acta Cytol.*, Vol. 19, No. 5, pp. 460-464 (1975); and M. A. Cambier, W. J. Christy, L. L. Wheeless, Jr. and I. N. Frank, "Slit-Scan Cytofluorometry Basis for Automated Prescreening of Urinary Tract Cytology", *J. Histochem. Cytochem.*, Vol. 24, No. 1, pp. 305-307 (1976).

In particular, from the Wheeless, Jr., Patten, Jr., and Cambier article entitled "Slit-Scan Cytofluorometry: Data Base for Automated Cytopathology", extensive investigation has shown that nuclear fluorescence from cells stained with Acridine Orange is higher in abnormal cells than in normal cells. The Cambier, Christy, Wheeless, Jr., and Frank article entitled "Slit-Scan Cytofluorometry Basis for Automated Prescreening of Urinary Tract Cytology", demonstrates potential usefulness in a slightly different area.

More recent slit-scan instruments utilize a flow cytofluorometer, details of which are described in: L. L. Wheeless, Jr., A. Hardy and N. Balasubramanian, "Slit-Scan Flow System for Automated Cytopathology", *Acta Cytol.*, Vol. 19, No. 1, pp. 45-52 (1975), also referenced above. This flow cytofluorometer implements the hybrid approach to defining a slit-producing aperture. In particular, secondary fluorescence is recorded from a cell as it flows through a thin "wall" of excitation illumination providing slit-excitation, and in addition slit-imaging is employed such that only the excited planar region is slit-imaged to a detector.

In this flow system, relatively transparent, fluorochrome stained cells in suspension ideally flow one-by-one through a focused slit of laser excitation light. Assuming the axis of flow is defined as the Z axis, in essence a planar sheet of excitation light in the X-Y plane is generated defining an excitation region. As the fluorochrome stained cells flow through the excitation region, fluorescence emissions are generated at the intersection of the planar excitation region and the cell. As the cell flows through the excitation region, a plurality of substantially planar parallel cross-sections of the cell along the Z axis are excited to secondary fluorescence. Monitoring the fluorescense emissions generates a slit-scan type contour along the Z axis.

It should be noted that one difference between systems wherein the slit is defined by optical imaging, and systems wherein the slit is defined by excitation illumination, relates to the difference in the shape of the aperture effective cross-section. In the optically-imaged slit-scan system, the aperture is a true slit. In the slit excitation system, the sheet of laser light has a Gaussian intensity distribution in the direction of flow (along the Z axis), and is elliptical in cross-section (in the X-Y plane). This difference, however, is insubstantial in practice, and the expression "slit-scan type contour" as employed herein is intended to refer interchangeably to contours generated by either of these approaches, and both are in fact employed at the same time in one embodiment of the present invention.

One particular problem in evaluating cells by means of a one-dimensional slit-scan type contour along a single axis is that false alarms may occur as a result of such factors as cell orientation and cell overlap. It has been determined that the majority of false alarms are due to either improper cell orientation, multinucleate cells, or overlapping cells oriented such that both nuclei enter the measurement region simultaneously. Such a cell or cells may be completely normal but, in particular orientations, process to greater nuclear fluorescence than uninuclear cells of the same cell type, and thus be erroneously classified as abnormal. Similarly, the entire cell may be oriented with the plane of the cell parallel to the plane of the slit excitation such that there is substantially no discrimination between cytoplasmic fluorescence and nuclear fluorescence. The problem of binucleate cells is discussed in particular in the literature reference: J. L. Cambier and L. L. Wheeless, Jr., "The Binucleate Cell: Implications for Automated Cytopathology", *Acta Cytol.*, Vol. 19, No. 3, pp. 281-285 (1975).

At least four general approaches to solving cell classification problems resulting from particular cellular orientations have been proposed. A first technique is the use of flow nozzles and analysis chambers which tend to produce a desired orientation of the cells. This general approach is suggested by the Hogg U.S. Pat. No. Re. 29,141, and in the literature reference: D. Kay and L. L. Wheeless, Jr., "Experimental Findings on Gynecologic Cell Orientation and dynamics for Three Flow Nozzle Geometries", *J. Histochem. Cytochem.*, Vol. 25, No. 7, pp. 870-874 (1977).

A second technique is to provide a second analysis stage which analyzes cells for which a positive event has been recorded as a result of passage through a first slit-scan type measurement stage. The second stage may employ a higher resolution analysis, and may obtain and analyze a two dimensional image. Such techniques are generally described in the following two literature references: L. L. Wheeless, Jr., D. B. Kay, M. A. Cambier, L. Cambier and S. F. Patten, Jr., "Imaging Systems for Correlation of False Alarms in Flow", *J. Histochem. Cytochem.*, Vol. 25, No. 7, pp. 864-869 (1977); and D. B. Kay, L. Cambier and L. L. Wheeless, Jr., "Imaging System for Correlating Fluorescence Cell Measurements in Flow", Proceedings of the Society of Photo-Optical Instrumentation Engineers, San Diego, Calif., Vol. 126, *Clever Optics*, pp. 132-139 (Aug. 25-26, 1977).

Third, and particularly in the context of a second analysis stage as mentioned immediately above, it has been suggested that a segmented slit technique would be useful. (Wheeless, Kay, Cambier, and Patten, "Imaging Systems for Correlation of False Alarms in Flow", above.) This technique produces a plurality of slit-scan type contours, each representing fluorescence across only a portion of the cell, and may be considered a low-resolution form of two-dimensional imagery.

Fourth, it has been recognized that apparatus which would provide one-dimensional slit-scan contours along three orthogonal axes would be quite useful in providing additional information useful in reducing the incidence of false alarms, particularly those resulting from binucleate or overlapping cells which are oriented such that, in a single slit-scan type contour, each appears to be an abnormal cell having a high nuclear fluorescence, rather than a binucleate cell or a pair of overlapping cells producing two distinct peaks on the slit-scan contour. In a multi-dimensional slit-scan flow system, in which three orthogonal projections of cell fluorescence are collected, overlapping cells produce three slit-scan contours. In at least one of these contours the nuclei will in most cases be evidenced by two distinct fluorescence peaks, which can be recognized as such, and the nuclear fluorescence measurement disregarded. The Cambier and Wheeless, Jr. article entitled "The Binucleate Cell: Implications for Automatic Cytopathology", cited above, itself refers to the desirability of a system employing three orthogonal slits. An additional such reference is in the Wheeless, Jr., Hardy and Balasubramanian article, also cited above, which describes a "Slit-Scan Flow System for Automated Cytopathology". A more recent analysis of false alarms may be found in L. L. Wheeless, Jr., J. L. Cambier, M. A. Cambier, D. B. Kay, L. L. Wightman and S. F. Patten, Jr., "False Alarms in a Slit-Scan Flow Systems: Causes and Occurrence Rates Implications and Potential Solutions", *J. Histochem. Cytochem.*, Vol. 27, No. 1, pp. 596–599 (1979).

The above-cited Kay, Wheeless, Jr. and Cambier U.S. Pat. No. 4,293,221 discloses various embodiments for obtaining multi-dimensional slit-scan type contours of biological cells in flow. In addition, similar multi-dimensional slit-scan flow systems are disclosed in the following literature references: J. L. Cambier, D. B. Kay and L. L. Wheeless, Jr., "A Multi-Dimensional Slit-Scan Flow System", *J. Histochem. Cytochem.*, Vol. 27, No. 1, pp. 321–324 (1979); D. B. Kay, J. L. Cambier and L. L. Wheeless, Jr., "Imaging in Flow", *J. Histochem. Cytochem.*, Vol. 27, No. 1, pp. 329–334 (1979); J. L. Cambier and L. L. Wheeless, Jr., "Predicted Performance of Single- versus Multiple-Slit Flow Systems", *J. Histochem. Cytochem.*, Vol. 27, No. 1, pp. 334–341 (1979); and L. L. Wheeless, Jr., J. L. Cambier, M. A. Cambier, D. B. Kay, L. L. Wightman and S. F. Patten, Jr., "False Alarms in a Slit-Scan Flow System: Causes and Occurrence Rates Implications and Potential Solutions", *J. Histochem. Cytochem.*, Vol. 27, No. 1, pp. 596–599 (1979).

In several embodiments, three (X, Y and Z axis) orthogonal one-dimensional projections of cell fluorescence are obtained. In one broad approach described in the above-cited Kay, Wheeless, Jr. and Cambier U.S. Pat. No. 4,293,221, fluorochrome stained cells in suspension flow one-by-one through a focused slit of laser excitation light. If the axis of flow is defined as the Z axis, in essence a planar sheet of excitation light in the X-Y plane is generated defining an excitation region. As the fluorochrome stained cells flow through the excitation region, fluorescence emissions are generated at the intersection of the planar excitation region and the cell. By monitoring the fluorescence emissions as the cell flows through the excitation regions, a plurality of substantially planar parallel cross-sections of the cell along the Z axis are excited to fluorescence, and a slit-scan type contour along the Z axis is generated. To generate slit-scan type contours along the cellular X and Y axes, various optical system embodiments, including side imaging and on-axis imaging approaches, effectively define various combinations of cellular linear portions within the Z axis cross-section. The fluorescence or other emissions from these cellular linear portions are then combined by employing an integration technique to generate the desired contours.

In another broad approach described in the above-cited Kay, Wheeless, Jr. and Cambier U.S. Pat. No. 4,293,221 with particular reference to FIGS. 15, 16 and 17 thereof, and one which is particularly relevant with respect to the present invention, a three-dimensional volume of a cell in flow is illuminated with exciting radiation which is not a narrow beam. Three slit-imaging optical systems view a central region in the flow stream, which central region is within the excited volume. The optical systems have three respective orthogonal axes symmetrically located about the stream and directed downward at an angle towards the axis of flow such that the axis of flow forms equal angles with each optical axis. Geometrically, it can be shown that each of the optical axis is angled with respect to the flow or Z-axis at an angle equal to arc tangent $1/\sqrt{2}$, which is approximately 35°. A slit field stop is employed in the image plane of each optical system, and each of the three slits is oriented to be parallel to each of the three planes respectively of an $X'$-$Y'$-$Z'$ coordinate system, so-termed because it is rotated with respect to the flow or Z-axis and with respect to the X-Y-Z coordinate system. Behind each slit field stop, a photomultiplier tube detects the imaged cell fluorescence through a suitable optical wavelength filter, and each slit thus provides a scanned signal spatially orthogonal to the others.

In operation, as a cell flows through the illuminated central region it in effect flows simultaneously through three slit regions. The output of each of the three photomultiplier tubes provides a slit-scan signal spatially orthogonal to the others. In contrast to the embodiments wherein each cell flows through a thin "wall" of excitation illumination, the entire cell is illuminated at once (or at least the volume required for all three slit regions), and the slit apertures are exclusively the result of imaging by the optical systems.

As described in the above-cited Kay, Wheeless, Jr. and Cambier U.S. Pat. No. 4,293,221 an advantage of this system is the simpler signal processing required, as no integration is required and all three slit-scan contours are generated in real time. A disadvantage is that lower resolution is achieved because a greater depth of focus is required (increased by approximately $\sqrt{2}$ compared to systems employing a planar sheet of laser excitation light and various optical systems for defining cellular linear portions). A further disadvantage is a lower signal-to-noise ratio due to lower numerical aperture optics required by the greater depth of focus, as is explained more fully hereinafter.

SUMMARY OF THE INVENTION

By the present invention, there is provided a three-dimensional slit-scan flow system of the type wherein the entire cell is illuminated at once (or at least the volume required for all three slit regions), and the slit apertures are the result of imaging by the optical system, rather than of the type wherein each cell flows through a thin "wall" of excitation illumination. Accordingly, the previously-known advantage of simpler signal processing in that no integration is required and all three slit-scan contours are generated in real time is realized. The present invention provides the additional advantage that the depth of focus is not increased by approximately $\sqrt{2}$, but rather the depth of focus is only that which is required to image across the width of the flow stream.

Additionally, by the present invention there is provided a two-stage system wherein a cell in flow first encounters a single Z-axis slit scan station, and then encounters an X'-Y'-Z' multidimensional slit-scan station. The two stations are closely spaced, and a simplified optical system employs at least one common element. In the operation of such a two-stage system, if the Z slit-scan contour processes to an alarm, then the X'-Y'-Z' contours are processed for a second look to determine whether the alarm can be rejected. It has been found that the Z slit-scan contour carries the needed information approximately 98% of the time, and the X'-Y'-Z' contour, with its necessarily more complex processing, is needed only approximately 2% of the time.

Briefly stated, and in accordance with one overall concept of the invention, it is recognized that a cell may be effectively partitioned into orthogonal substantially planar cross sections by means of optical imaging through three slit-imaging optical systems, with each of the optical imaging systems viewing the illuminated central region of the cell. Significantly, all optical axes lie substantially in a plane perpendicular to the flow axis, (although reasonable angular variations from the plane can be tolerated). Unlike the previous apparatus wherein the three optical axes are symetrically located about the flow stream and angled downwardly at an angle of approximately 35° with respect to the flow axis and therefore necessarily not lying in a single plane, each of the three imaging systems images directly across the flow stream. As a result, a lesser depth of focus is required.

The significance of this narrower depth of focus is that it can be directly traded for a desirable increase in system resolution.

More particularly, the depth of focus $\delta$ of an optical lens system may be expressed as:

$$\delta = \frac{\delta\sqrt{n^2 - (N.A.)^2}}{(N.A.)^2} \quad (1)$$

where:

$\lambda$ is the wavelength of light imaged, n is the refractive index of the immersion fluid in the space between the cell and objective lens, and N.A. is the numerical aperture of the lens.

Additionally pertinent is the following expression for resolution, given in terms of its inverse, $\Delta$, which is the dimension of the smallest detail which can be resolved. A smaller $\Delta$ indicates higher resolution. This expression is applicable for a well-corrected microscope objective lens operating diffraction limited:

$$\Delta = \frac{0.61\lambda}{N.A.} \quad (2)$$

Equation (1) and Equation (2) may be combined to show that $\delta$ is approximately proportional to $\Delta^2$ and therefore decreasing the depth of focus ($\delta$) increases the resolution (smaller $\Delta$).

From Equation (2) it can be seen that $\Delta$ is related to the numerical aperture N.A., which is a determining factor in light collection capability and therefore signal-to-noise ratio. It will accordingly be appreciated that minimizing the depth of focus $\delta$ requirement is a significant advantage of the present invention in terms of performance.

In order to partition the cell into orthogonal substantially planar cross-sections by means of slit-imaging in accordance with the invention, three optical systems having three respective optical axes are employed. For a symmetrical system, the three optical axes are angularly spaced at 120° within the plane perpendicular to the flow axis. Further, in a symmetrical system, it can geometrically be shown that the plane of each of the slit-imaged portions in the central region intersects the plane perpendicular to the flow access at an angle substantially equal to arc tangent $\sqrt{2}$, which is approximately 55°. This may readily be accomplished by means of a slit field stop in an image plane of each of the respective systems, with the slit field stops correspondingly angled at approximately 55° with respect to the plane perpendicular to the flow axes.

Briefly stated, and in accordance with another overall concept of the invention, a two-stage flow cytofluorometer for sequentially obtaining a one-dimensional slit-scan type fluorescence contour and multidimensional slit-scan type fluorescence contours may readily be provided by means of an optical system wherein one of the objective lenses of any one of the X'-, Y'-, Z'- axis slit-imaging systems may be shared to, in addition, generate a one-dimensional slit-scan type fluorescence contour along the Z or flow axis. This is accomplished by providing, in addition to the volume laser light illumination, a slit-type laser excitation beam immediately upstream of the illuminated volume, with a second optical axis slightly angled with respect to the slit-imaging optical axis to view the resultant planar excited region.

Briefly stated, and in accordance with a more particular aspect of the invention, a flow cytofluorometer for obtaining multidimensional slit-scan type fluorescence contours of a biological cell includes means for conveying the cell along a flow axis, and an illumination system providing a beam of electromagnetic radiation for exciting secondary fluorescence in the cell, the beam focus being such that a central region along the flow axis is illuminated and a volume of the cell is excited to fluorescence as the cell passes through the illuminated region. A plurality of imaging systems are provided for slit-imaging across the central region, each of the imaging systems viewing the central region along a respective optical axis, with the optical axes all lying substantially in a plane perpendicular to the flow axis. The planes of the resultant slit-imaged portions in the central region are non-parallel with each other and non-parallel with the flow axis. Lastly, a photodetector element, such as a photomultiplier tube with suitable optical bandpass filtering, is coupled to each of the imaging systems for responding to fluorescence from each of the slit-imaged portions in the central region. Thus, each of the photodetector elements outputs a slit-scan type contour in real time along a cellular axis perpendicular to the plane of the respective slit-imaged portion.

While the preferred geometrical arrangement is an entirely symmetrical one as may be visualized by analogy to a cube standing on one corner, significant variation is possible with little adverse effect on the results. In particular, the cube visualized by analogy may be tilted. In such event, three othogonal planes can still be defined by slit imaging along three optical axes all lying substantially in a plane perpendicular to the flow or Z axis. However, the angular spacing within the plane between the three axes will no longer be symmetrical, and will no longer be 120°. Also, the angles of the defined planes with respect to the flow axis will no longer be equal, and will no longer be equal to arc tangent $\sqrt{2}$.

In addition, while an entirely orthogonal relationship between the planes is preferred for most meaningful data, variation is possible. Similarly, for fabrication reasons or otherwise, the three axes might not all be perfectly in the same plane, but only substantially so. What is important is that imaging be essentially across the flow stream to require the lowest possible depth of focus, rather than obliquely. Such a variation is in fact employed in the particular embodiment of a two-stage system described hereinafter.

Briefly stated, and in accordance with another, more particular, aspect of the invention, a two-stage flow cytofluorometer is provided for sequentially obtaining a one-dimensional slit-scan type fluorescence contour of a biological cell and multi-dimensional slit-scan type fluorescence contours of the cell. The two-stage flow cytofluorometer includes means for conveying the cell along a flow axis, and an illumination system including elements providing a substantially planar beam of electromagnetic radiation illuminating a planar region along the flow axis, thus providing a "wall" of excitation illumination for exciting secondary fluorescence in the cell, the flow axis intersecting but not lying within the plane of the beam such that the cell passes through the beam in a plurality of substantially planar parallel cross-sections of the cell are successively excited to secondary fluorescence. The illumination system additionally includes elements providing a substantially cylindrical beam of electromagnetic radiation immediately down stream of the substantially planar beam for exciting secondary fluorescence in the cell, the cylindrical beam focus being such that a central region along the flow axis is illuminated and a volume of the cell is excited to fluorescence as the cell passes through the illuminated region. A plurality of imaging systems each have an objective lens, and each of the imaging systems includes first optical axis elements for slit imaging through the respective objective lens across the central region, the first optical axes all lying substantially in a plane perpendicular to the flow axis and intersecting within the central region, the planes of the resultant slit-imaged portions in the central region being non-parallel with each other and non-parallel with the flow axis. In addition, one of the imaging systems further includes second optical axis elements for imaging the planar region through the respective objective lens, the second optical axis being angled with respect to the respective first optical axis in a plane perpendicular to the flow axis. To provide the single-dimensional Z-axis slit-scan contour, a photodetector element is coupled to the second optical axis elements for responding to secondary fluorescence from the successively excited cellular cross sections as a cell passes through the substantially planar beam. For developing the multi-dimensional X'-Y'-Z' slit-scan contours, a photodetector element is coupled to each of the first optical axis elements for responding to fluorescence from each of the slit-imaged portions in a central regions.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings in which:

DESCRIPTION OF THE PREFERRED EMBODIMENTS

Preliminarily, it should be noted that while the particular apparatus described in detail herein is for analyzing cellular or biological particles, this is for purposes of illustration only, and the invention may be employed for analyzing particles of other types as well.

Figure 1:
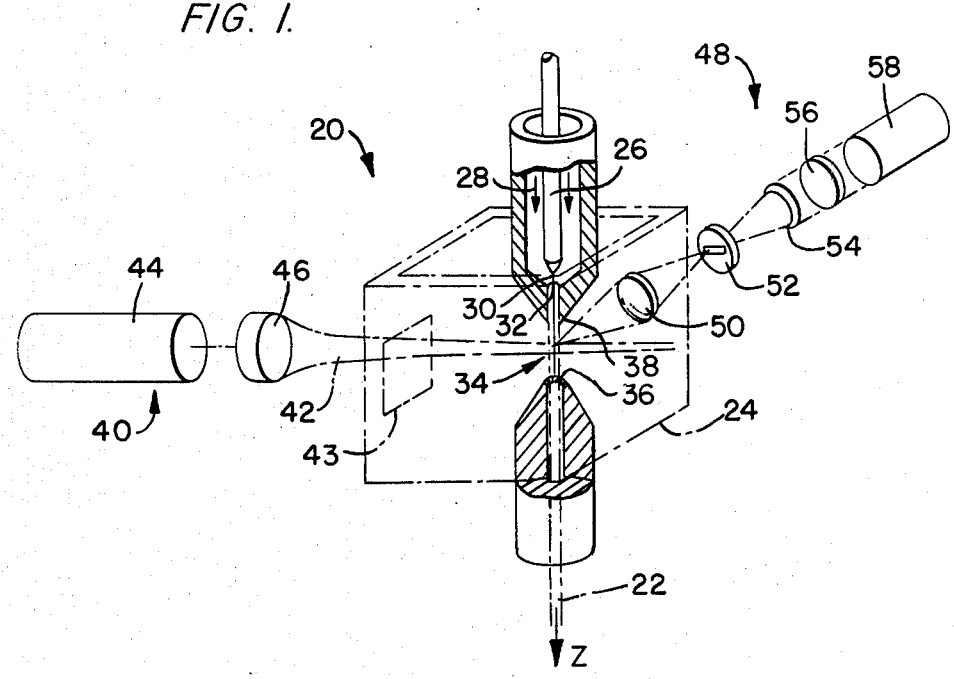
FIG. 1 is a highly schematic perspective view of a single-axis slit-scan flow cytofluorometer of the type which generally illuminates a central region of a flow stream, and which employs optical slit imaging.

Referring first to FIG. 1, there is shown in diagrammatic form a one-dimensional slit-scan flow cytofluorometer 20 of the type wherein a volume of the cell is illuminated and the slit-producing aperture is defined by optical imaging. While the FIG. 1 cytofluorometer 20 does not embody the invention, it is believed that preliminary description thereof will be useful in understanding the present invention.

For conveying cells along a flow axis 22 (Z axis), a flow chamber 24 employing a sheath flow geometry is employed. Fluorochrome (Adridine Orange) stained cells in suspension enter the chamber 24 via an axial specimen tube 26 and are enveloped in a coaxial sheath of water 28. A stream 30 of cells in suspension exits the specimen tube 26 and is constricted in a flow nozzle 32. At this point, the cell stream 30 has a diameter which is approximately that of the individual cells.

The cell stream 30 flows across a gap region 34, and exits the chamber 24 via a capillary tube 36. The gap region 34 is typically 200-350 micrometers from the exit 38 of the flow nozzle 32 to the entrance of the capillary tube 36, with a typical flow rate of from 20 to 100 cm/sec. The flow is laminar in the capillary tubes 26 and 36. Preferably, the flow nozzle is designed to align cells in the direction of flow, and produces a cell stream 30 having an elongated cross-section. For further information concerning such sheath flow nozzles, the references D. B. Kay and L. L. Wheeless, Jr., "Experimental Findings on Gynecologic Cell Orientation and Dynamics for Three Flow Nozzle Geometries", *J. Histochem. Cytochem.*, Vol. 25, No. 7, pp. 870-874 (1977) and M. J. Fulwyler, "Hydrodynamic Orientation of Cells", *J. Histochem. Cytochem.*, Vol. 25, No. 7, pp. 781-783 (1977) may be consulted.

In FIG. 1, an illumination system, generally designated 40, provides a generally cylindrical beam of electromagnetic radiation 42 for exciting secondary fluorescence in cells carried by the flow stream 30, entering the chamber 24 through a suitable window 43. The focus of the beam 42 is such that a central region along the flow axis 22 is illuminated and a volume of each cell is excited to fluorescence as the cell passes through the illuminated region. More particularly, the illumination system 40 comprises an approximately 1.0 watt, 488 nanometer argon-ion laser 44 brought to suitable circular beam focus by means of an optical system 46 which includes a spatial filter.

As is known, the cross-section of a laser beam has a non-uniform (specifically, Gaussian) intensity distribution. It is preferred, however, that the beam 42 be well-collimated with a more nearly uniform cross-sectional intensity distribution for substantially uniform cell illumination. To accomplish this, the beam is initially expanded, and the relatively uniform center portion only is selected by means of a suitable aperture arrangement.

For providing a Z axis slit-scan contour as cells flow through the beam 42, a single dimension slit-imaging system 48 comprises a microscope objective 50 projecting into the chamber 24 and including one or more individual lens elements, followed by a slit field stop 52 in the image plane, a lens 54, a band pass filter 56 for transmitting only fluorescent radiation of a selected wave length and discriminating against the wave length of the laser 44, and a photomultiplier tube 58 which serves as the actual detector element. Because of the band pass filter 56, the photomultiplier tube 58 responds only to fluorescence, and not the laser illumination. In the slit-imaging system 48, the slit field stop 52 is oriented perpendicularly to the Z-axis 22 such that a planar region of the flow stream 30 is imaged. In particular, the objective 50 images the slit field stop 52 to the flow stream 30.

A prior art alternative essentially equivalent to FIG. 1 employs a thin 4.0 micrometer slit of 488 nanometer wavelength excitation illumination from an argon-ion laser, and fluorescence from the entire excited region is collected. This eliminates the need for a slit-imaging system.

It will be appreciated that the FIG. 1 depiction is highly schematic one which, for clarity of illustration, omits some important design details. In particular, due to the cylindrical shape of the cell stream 30, significant aberrations would occur in an optical system which employed fluid-to-air and air-to-glass interfaces. One approach to minimizing such aberations would be a custom design optical system.

An alternative and preferred method of circumventing the need for such custom lens design is to eliminate the optical interfaces by employing a water immersion microscope objective lens protruding into the fluid environment. This approach is described in the above-incorporated commonly-assigned Kay, Wheeless, Jr., and Cambier U.S. Pat. No. 4,293,221, and additionally in the literature reference D. B. Kay, J. L. Cambier and L. L. Wheeless, Jr., "Imaging in Flow", *J. Histochem. Cytochem.*, Vol. 27, No. 1, pp. 329-334 (1979).

Figure 2:
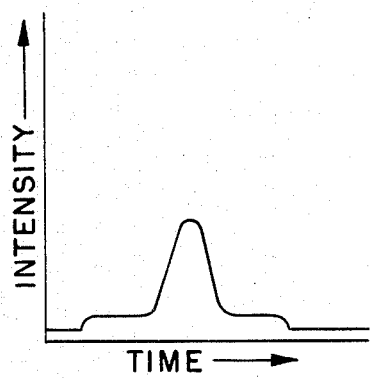
FIG. 2 is a graph showing a typical slit-scan type contour such as will be produced by a cell flowing along the flow axis (Z axis) of the cytofluorometer shown schematically in FIG. 1.

FIG. 2 illustrates a typical one-dimensional slit-scan type contour such as is generated at the output of the photo-multiplier tube 58 in the cytofluorometer of FIG. 1 as a single cell passes through the excitation laser beam 42 and the secondary fluorescence from successive cross-sections is imaged. The hump of the FIG. 2 curve represents the nuclear fluorescence, while the shoulders represent the cytoplasmic fluorescence. As is discussed in greater detail in the literature and patents mentioned in the "Background of the Invention," useful information concerning the cells, such as nuclear fluorescence and nuclear to cytoplasmic (N/C) ratio, may be derived from such a contour.

The slit-scan flow system of FIG. 1 generates a slit-scan type contour along only a single axis. In the illustrated case where the plane of slit imaging system 48 is perpendicular to the flow or Z axis, the slit-scan type contour as represented by FIG. 2 may be termed a slit-scan contour along the Z-axis or flow axis.

Figure 3:
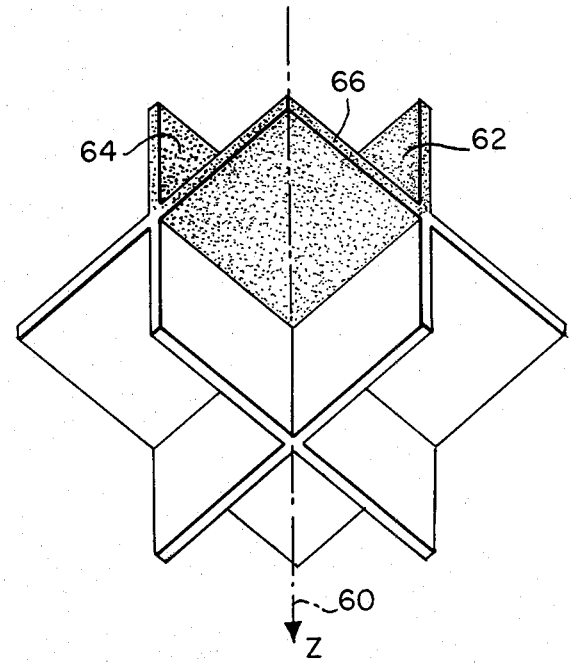
FIG. 3 is a highly schematic representation of the manner in which a cell may be optically partitioned into orthogonal substantially planar cross-sections in accordance with the invention.

Referring now to FIG. 3, the manner in which a cell is effectively partitioned into substantially planar cellular cross-sections by multi-dimensional flow cytofluorometers according to the present invention is depicted. The partitioning depicted in FIG. 3 is substantially identical to that depicted in FIG. 15 of the above-referenced Kay, Wheeless, Jr. and Cambier U.S. Pat. No. 4,293,221.

In FIG. 3, cells flow along a Z or flow axis 60. However, a rotated coordinate system, herein termed an X'-Y'-Z' coordinate system is employed, the cell partitioning being into three orthogonal substantially planar cross sections 62, 64 and 66. Each of the planar cross sections 62, 64 and 66 forms an equal angle with the flow axis 60, which angle may geometically be shown to be equal to arc tangent $(1/\sqrt{2})$. When computed, this angle is approximately 35°.

In accordance with the present invention, it is recognized that partitioning such as is depicted in FIG. 3 may be accomplished by slit-imaging along three optical axes all lying in a plane perpendicular to the Z axis 60, with the result that the depth of focus required is only that necessary to image across the flow stream 30, rather than obliquely as in the corresponding embodiment of the above-referenced Kay, Wheeless, Jr. and Cambier U.S. Pat. No. 4,293,221.

Figure 4:
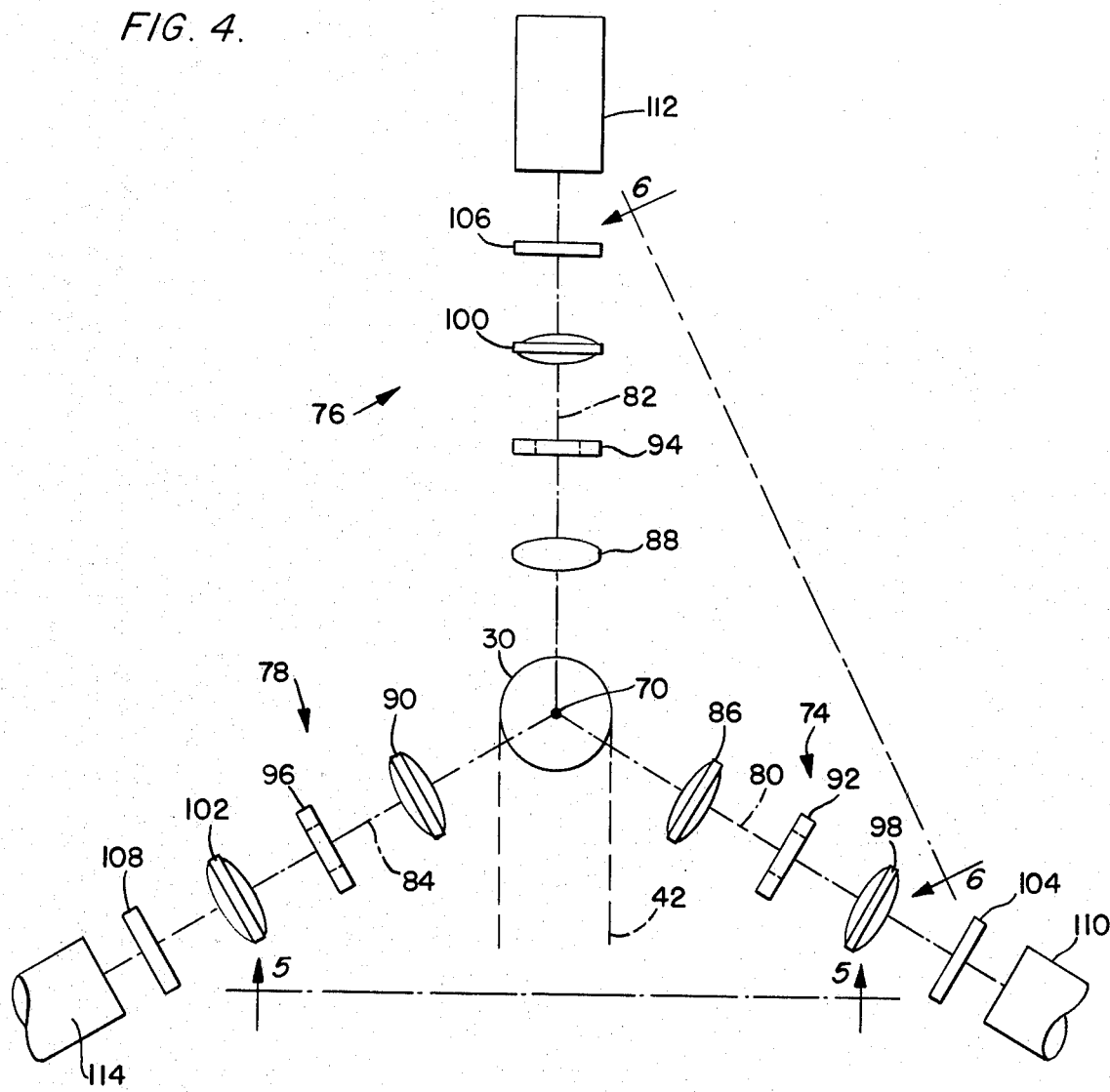
FIG. 4 is a top view of the flow cytofluorometer according to the invention for producing slit-scan contours in the orientations illustrated in FIG. 3.
Figure 5:
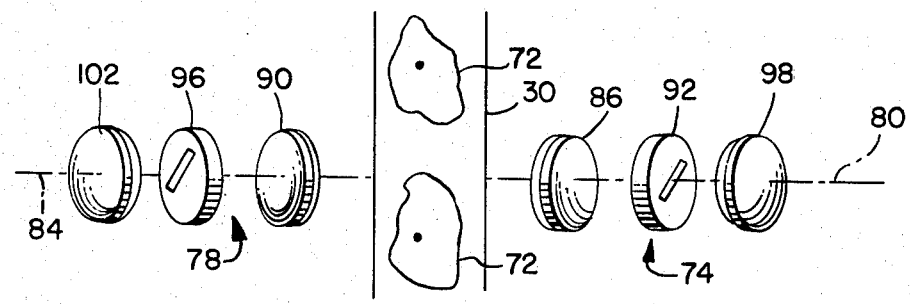
FIG. 5 is a side elevational view along line 5—5 of FIG. 4.
Figure 6:
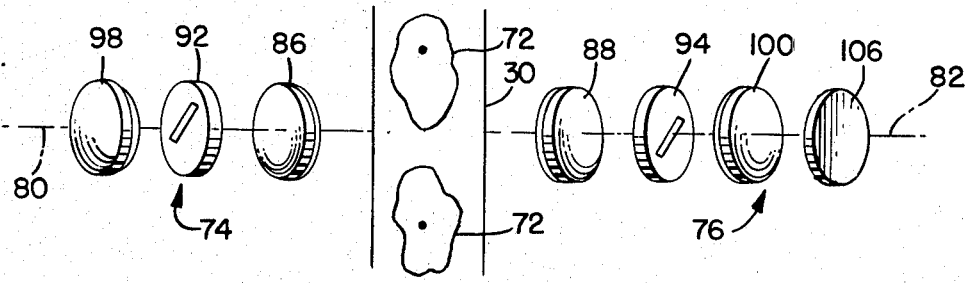
FIG. 6 is a similar side elevation along line 6—6 of FIG. 4.
Figure 7:
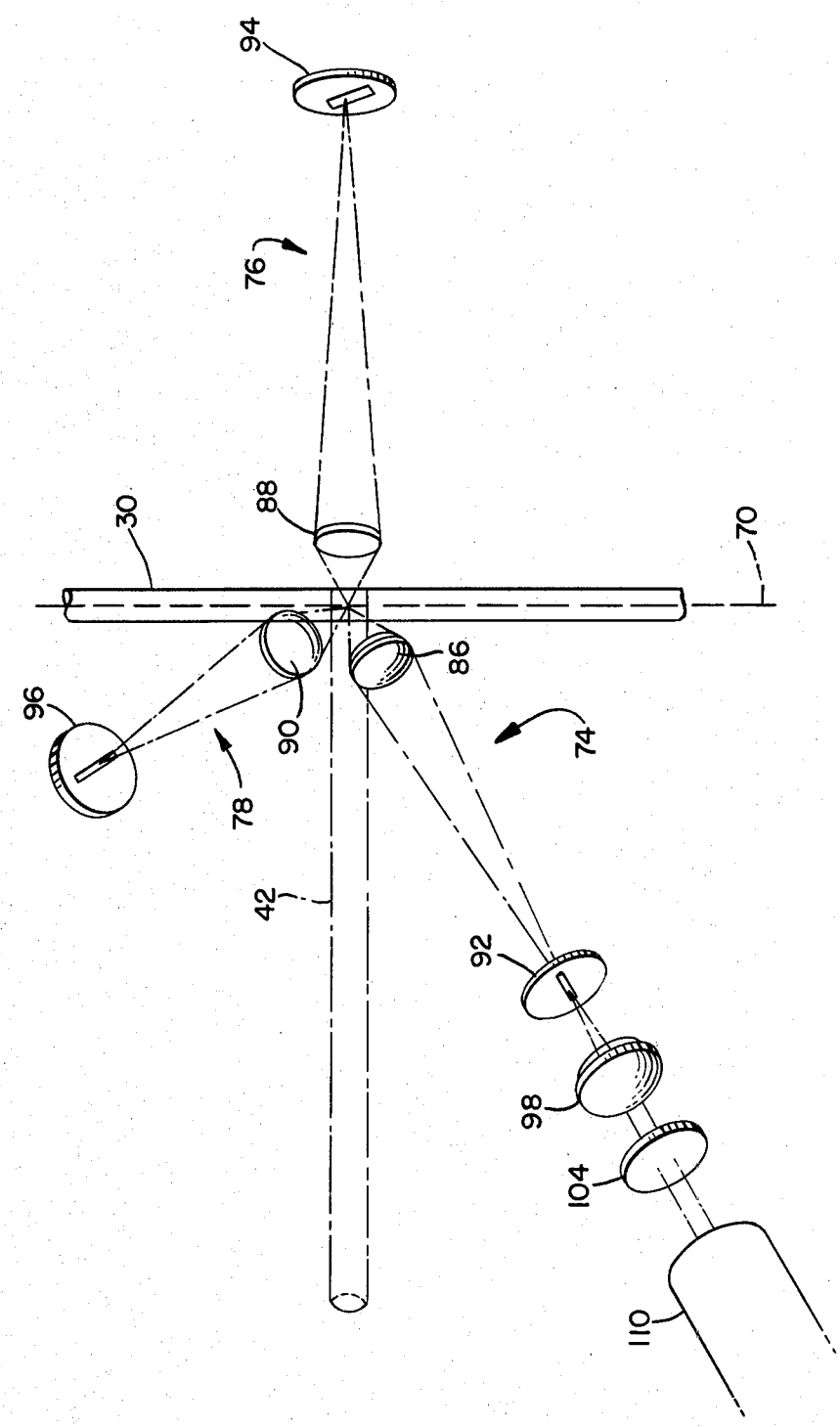
FIG. 7 is a perspective view of the flow cytofluorometer of FIGS. 4, 5 and 6.

Referring now to FIGS. 4, 5, 6 and 7, the preferred geometry of a system in accordance with the present invention is illustrated in highly schematic form. FIG. 4 is a top view looking down along the flow or Z axis 70, FIGS. 5 and 6 are side elevational views taken respectively on line 5—5 and 6—6 of FIG. 4 perpendicular to the flow axis 70, and FIG. 7 is a perspective view.

In the embodiment of FIGS. 4, 5, 6 and 7, the illumination and flow systems are substantially identical to those depicted in FIG. 1, and the details of the laser illumination and flow systems are accordingly omitted from FIGS. 4, 5, 6 and 7 for clarity of illustration. In FIGS. 4, 5, 6 and 7, the flow stream 30 is greatly enlarged compared to FIG. 1, and individual cells 72 carried therein are visible. It will be appreciated, however, that in FIGS. 4, 5, 6 and 7, the beam 42 of laser radiation substantially uniformly illuminates a central region along the flow axis 70 for exciting cells to secondary fluorescence.

In accordance with the invention, three optical systems 74, 76, and 78 slit-image across the central region illuminated by the laser beam 42. Each of the imaging systems 74, 76 and 78 views the central region along respective optical axes 80, 82 and 84, with the optical axes 80, 82 and 84 all lying substantially in a plane perpendicular to the flow or Z axis 70, as may clearly be seen from the side elevational views of FIGS. 5 and 6 taken along lines 5—5 and 6—6 of FIG. 4, respectively.

The imaging systems 74, 76 and 78 are all substantially identical and have the same number of elements, although some elements are omitted in several of the views. In particular, the imaging systems 74, 76 and 78 have respective microscopic objective lenses 86, 88 and 90 and respective slit field stops 92, 94, and 96. The lenses 86, 88 and 90 image the slits of the stops 92, 94, and 96 respectively to the flow stream 30, with the depth of focus required being that of the approximately fifty micrometer diameter of the flow stream 30. The imaging systems additionally have respective collimating lenses 98, 100 and 102, followed by band pass filters 104, 106 and 108 which serve to pass the 540 nanometer or other desired wavelength of secondary fluorescence, while blocking the 488 nanometer excitation wavelength of the illuminating laser beam 42. Lastly, photomultiplier tubes 110, 112 and 114 respond to the imaged secondary fluorescence.

While the flow cytofluorometer of FIGS. 4, 5, 6 and 7 will function with other geometries, it is highly preferred that the geometry be set up such that three symmetrical and mutually orthogonal planar slit-imaged portions be defined in the central region by imaging the respective slit field stops 72, 74 and 76 to the flow stream 30 by means of the objectives 86, 88 and 90. To accomplish this, the optical axes 80, 82 and 84 are evenly angularly spaced at 120° within the plane perpendicular to the Z or flow axis 70. Additionally, each of the slits of the slit field stops 92, 94 and 96 is properly angled so as to image a respective planar region within the flow stream 30, with the respective planar regions 62, 64 and 66 of FIG. 3 all being perpendicular. By geometrical analysis of a cube standing symmetrically on one corner, the required angle, with respect to the plane of the three optical axes 80, 82 and 84, can be determined to be equal to the arc tangent $\sqrt{2}$. Arc tangent $\sqrt{2}$ is approximately equal to 55°. Alternatively, with respect to the Z axis 70, each of the slit field stops 92, 94 and 96 is angled at an angle equal to arc tangent $(1/\sqrt{2})$. Arc tangent $(1/\sqrt{2})$ is approximately equal to 35°.

In the operation of the embodiment of FIGS. 4, 5, 6 and 7, as each of the cells 72 flows through the region illuminated by the laser beam 42 and imaged by the imaging system 74, 76 and 78, it in effect flows simultaneously through three slit volumes in orthogonal relationship to each other. Fluorescence produced in the slit volumes is imaged to the slit apertures 92, 94 and 96 and quasi-collimated by lenses 98, 100 and 102, band pass filtered in filters 104, 106 and 108 and then detected by the photomultiplier tubes 110, 112 and 114. The output of each of the photomultiplier tubes 110, 112 and 114 provides a slit-scan signal spatially orthogonal to the others.

Figure 8:
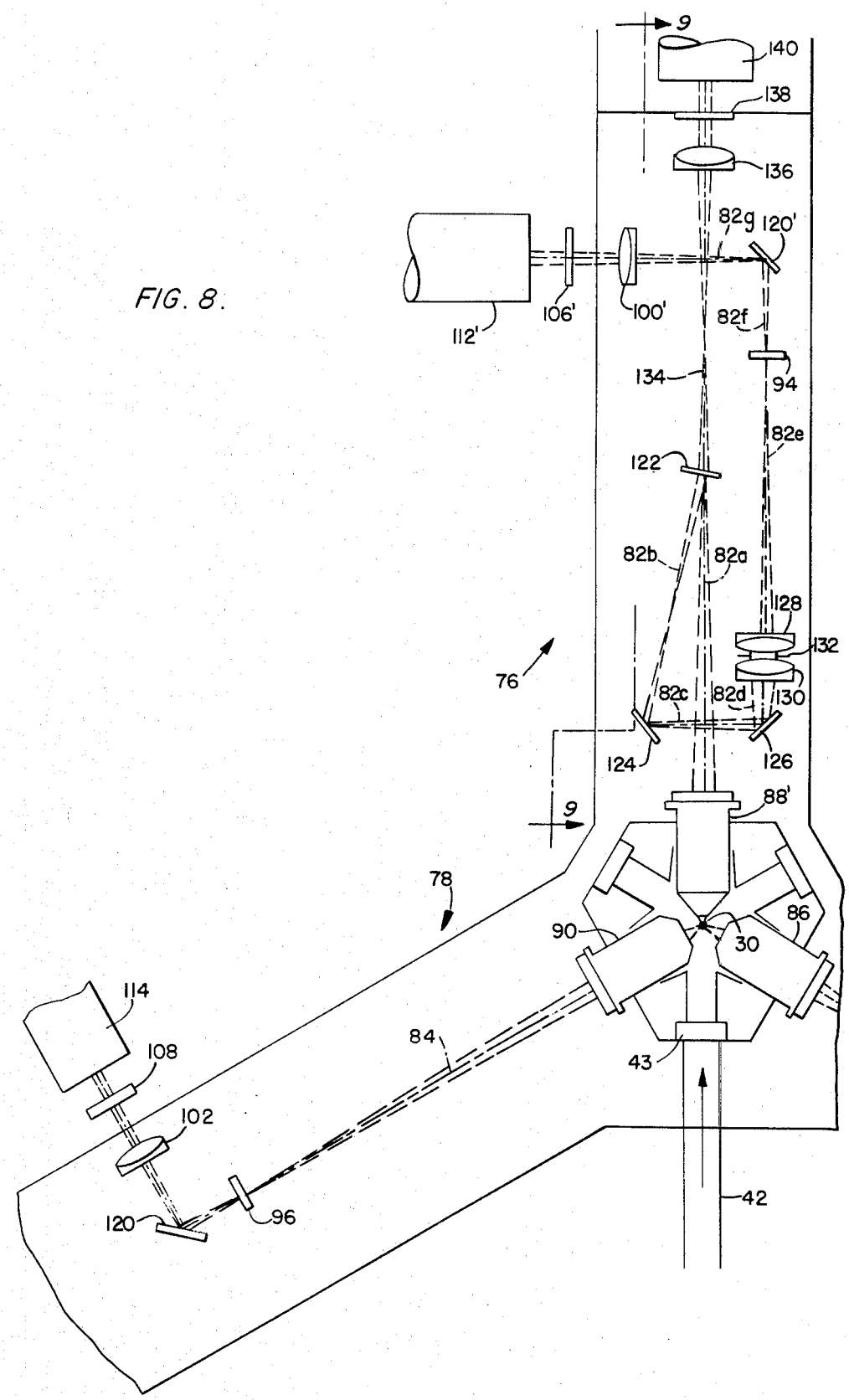
FIG. 8 is a top view of a two-stage flow cytofluorometer according to the ivention for sequentially obtaining a one-dimensional slit-scan type fluorescence contour and multi-dimensional slit-scan type fluorescence contours.
Figure 9:
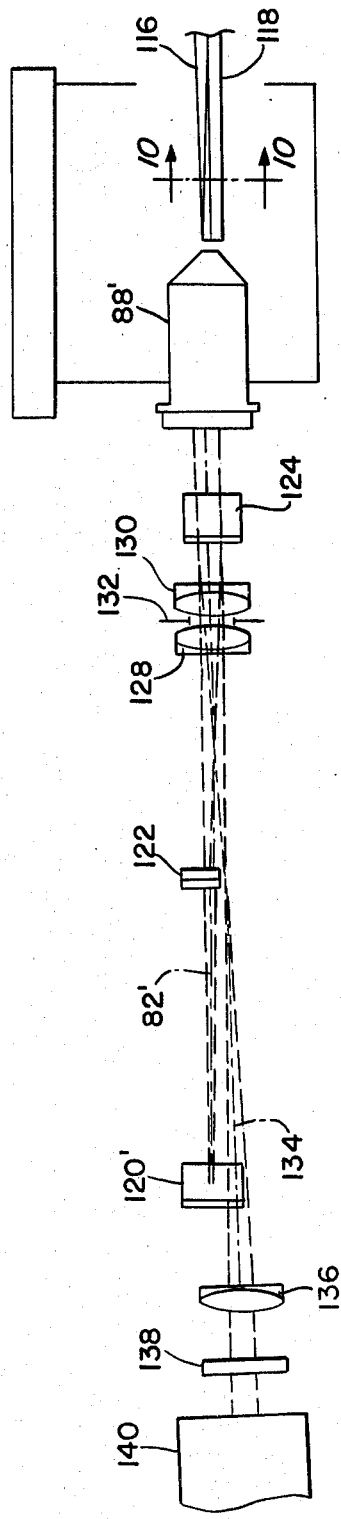
FIG. 9 is an elevational cross-section along line 9—9 of FIG. 8.
Figure 10:
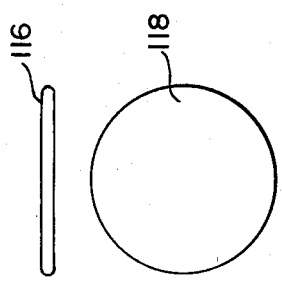
FIG. 10 is a section on line 10—10 of FIG. 9 showing the cross-sections of a substantially planar (actually elliptical cross-section) beam of laser illumination and a substantially cylindrical beam of laser radiation.

Referring now to FIGS. 8, 9 and 10, there is illustrated another embodiment of the invention in the form of a two-stage flow cytofluorometer which advantageously provides, in sequence, both a one-dimensional Z axis slit-scan type fluorescence contour at a first station and a three-dimensional X'-Y'-Z' slit-scan type fluorescence contour at a second station, the second station corresponding to the system described above with reference to FIGS. 4-7. FIGS. 8 and 9 provide significant additional detail compared to FIGS. 4, 5, 6 and 7, which additional detail may be directly applied to a better understanding of FIGS. 4, 5, 6 and 7.

The apparatus of FIGS. 8 and 9 may be considered as an extension of the apparatus of FIGS. 4-7, with the addition of a one-dimensional Z axis slit-producing aperture defined by excitation illumination. Accordingly identical reference numerals are applied to similar or corresponding elements in the two embodiments. FIG. 8 is a top view which may be compared generally to FIG. 4, while FIG. 9 is a side elevation taken along line 9—9 of FIG. 8 showing details of diverging optical paths which are utilized in order that the objective 88 may serve two purposes. FIG. 10 is a cross section on line 10—10 of FIG. 9 showing a line-focused (actually elliptical) approximately eighty milliwatt laser beam 116 defining a first measurement station positioned above an approximately one watt circular laser beam 118 illuminating a substantial cell volume.

The slit beam 116 and circular beam 118 are produced from a single laser employing conventional beam-splitting techniques. For the slit beam 116 illuminating the first measurement station, light is taken directly from the laser (not shown), through a spatial filter, a cylindrical lens (not shown), followed by a collimating lens. For the circular beam 118, a beam splitter (not shown) separates a portion of the laser light just prior to the cylindrical lens. The separated beam is expanded to proper size, and brought to focus at the front focal plane of the collimating lens. From this front focal plane, the circular beam diverges to the collimating lens, to emerge as the collimated circular beam 118.

Referring to FIG. 8 in greater detail, the two imaging systems 74 and 78 of lesser complexity include the respective slit field stops 92 (not shown in FIG. 8) and 96 imaged by means of objectives 86 and 90 across the flow stream 30 (FIGS. 4-7). The two optical axes 80 and 84 are, for convenience, bent by means of mirrors such as the exemplary mirror 120 prior to the collimating lenses 98 and 102. It will be appreciated, however, that the mirror 120 does not affect the basic principle that the optical axes 80 and 84 effectively lie substantially within a plane perpendicular to the flow axis.

For the purpose of distinguishing between those elements of the optical system which slit image across the central region at the second measurement station illuminated by the circular cross section laser beam 118 from those optical axis elements for imaging the slit-illuminated first measurement station, the optical axis elements associated with the three-slit imaging systems are herein referred to as first optical axis elements, and those associated with imaging the slit-excited region are herein referred to as second optical axis elements, although the imaging system 76 only, and not the imaging systems 74 and 78 includes the second optical axis elements.

concerning the details of the objectives 86 and 90, these objectives are water-immersion microscope objective lenses having a 10× magnification and a numerical aperture (N.A.) of 0.25. (The N.A. for the objective lenses imaging the cell to the slit field stops 92, 94 and 96 is determined by the depth of focus δ required as determined by taking into account the typical cell 72 dimension and flow stream 30 diameter. Typical cell dimensions are approximately 50 micrometers maximum. With a depth of focus δ of $50 \times 10^{-6}$ meters, and assuming a fluorescence wavelength λ of $540 \times 10^{-9}$ meters, and a refractive index, n, of 1.33 (that of water), from Equation (1), provided hereinabove under the heading "Summary of the Invention", N.A. may be calculated to be in the order of approximately 0.12. However, preliminary experimental studies indicate that good results can be obtained with an N.A. of 0.25. This means a little defocus is occurring, a 0.25 N.A. objective lens having a depth of focus of only $11.5 \times 10^{-6}$ meters.)

With reference now to FIGS. 9 and 10 in addition to FIG. 8, the remaining, dual-purpose, optical system 76 will now be described. As several of the corresponding elements are not absolutely identical to those of the optical systems 74 and 78, elements of the dual-purpose optical system 76 are denoted by primed reference numerals. Consistent with its dual purposes, the optical system 76 has first optical axis elements for slit imaging the central region illuminated by the round cross-section laser beam 118 defining the second measurement station, and second optical axis elements for imaging the slit-illuminated region defining the first measurement station. The systems, however, share a common water-immersion microscope objective lens 88'. To accomodate two stations, the gap region 34 (FIG. 1) is increased to approximately 900 micrometers in the embodiment of FIGS. 8, 9 and 10.

In order to obtain high signal-to-noise ratio one-dimensional contours, the objective lens 88' differs from the objective lenses 86 and 90 in that its N.A. is higher, specifically 0.40. Since the slit aperture at the first measurement station is defined by excitation illumination, light collection capability only, and not any particular depth of focus, is required for the first measurement station.

The first optical axis elements for slit imaging across the central region will be considered first, these elements functioning essentially identically to those of the optical systems 74 and 78. The slit 94' is imaged through the microscope objective lens 88' to the central region, but the direction of the optical path 82' is folded, by means of mirrors 122, 124 and 126, in order to accommodate the physically longer path length required. Additionally, in order for this portion of the system to be optically equivalent to that associated with the optical axes 80 and 84 of the systems 74 and 78, a relay optical system having a magnification of 1.0 and comprising a pair of lenses 128 and 130 is provided, with an intermediate iris 132 to reduce the N.A. to 0.25, that of the other objectives 86 and 90. The first optical axis 82' then comprises six segments designated 82a, 82b, 82c, 82e, 82f and 82g.

In order to image, or at least collect light from, the planar region excited by the line focused beam 116, second optical axis elements aligned along an optical axis 134 are provided. The second optical axis elements comprise a collimating lens 136, a band pass filter 138, and a photomultiplier tube 140 which serves as a detector. The second optical axis 134 is angled with respect to the first optical axis 82' in order to image the first station, which physically is slightly above the second station. Thus, there is no interference between the two optical paths along the respective axes 82' and 134.

Actually, in the embodiment illustrated, neither of the optical axes 82' or 134 lies exactly within the plane perpendicular to the Z axis. The first optical axis 82' with elements for slit-imaging the second station is angled approximately 2.5° above this plane (but still essentially imaging across the flow stream 30), and the second optical axis 134 with elements for collecting fluorescence from the slit-excited first station is angled approximately 2.5° below the plane. The common objective lens 88' has an 880 micrometer field of view, and is aligned along the plane perpendicular to the flow axis.

In the operation of the system of FIGS. 8, 9 and 10, cells 72 flow sequentially past the first imaging station defined by the line focused laser beam whereat the secondary fluorescence from the entire slit excitation region is collected by the photomultiplier tube 140, and then past the second measurement station which comprises the three-dimensional mutually orthogonal X'-Y'-Z' slit-imaging system as described hereinabove with reference to FIGS. 4-7. The spacing between the two measurement stations is in the order of 0.5 millimeters to 1.0 millimeters.

If the Z slit scan contour processes to an alarm, then the X'-Y'-Z' contours are processed for a second look to determine whether the alarm can be rejected. The Z slit scan contour from the first measurement station carries the needed information approximately 98% of the time, and the X'-Y'-Z' contours from the second measurement station are needed only approximately 2% of the time.

From the foregoing, it will be appreciated that there has been provided an improved multidimensional slit-scan flow system, including two-stage measurement capability. The analysis systems to which the optical systems herein described are connected are not a part of the subject invention, as a variety of analysis techniques may be employed and are currently being developed. However, one such system is briefly described in the above-referenced Kay, Wheeless, Jr. and Cambier U.S. Pat. No. 4,293,221 as well as in various of the literature references cited.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A flow fluorometer for obtaining multidimensional slit-scan type fluorescence contours of a particle, comprising:

means for conveying the particle along a flow axis;

an illumination system providing a beam of electromagnetic radiation for exciting secondary fluorescence in the particle, the beam focus being such that a central region along the flow axis is illuminated and a volume of the particle is excited to fluorescence as the particle passes through the illuminated region;

a plurality of imaging systems for slit imaging across the central region, each of said imaging systems viewing the central region along a respective optical axis, with said optical axes all lying substantially in a plane perpendicular to said flow axis, and the planes of the resultant slit-imaged portions in the central region being non-parallel with each other and non-parallel with said flow axis; and a photodetector element coupled to each of said imaging systems for responding to fluorescence from each of the slit-imaged portions in the central region, each of said photodetector elements outputting a slit-scan type contour along a particle axis perpendicular to the plane of the respective slit-imaged portion.

2. A flow fluorometer according to claim 1, which comprises three slit-imaging systems defining three mutually orthogonal planar slit-imaged portions in the central region.

3. A flow fluorometer according to claim 1, wherein:
said means for conveying the particle along a flow axis comprises a flow stream of liquid within which the particle is carried; and wherein
said illumination system comprises a laser providing a beam spread at least sufficiently to illuminate a central region through which particles flow along the flow axis.

4. A flow fluorometer according to claim 3, wherein said laser provides a beam which substantially uniformly illuminates the central region.

5. A flow fluorometer according to claim 1, which comprises three slit imaging systems and wherein said optical axes are angularly spaced at 120° within said perpendicular plane.

6. A flow fluorometer according to claim 5, wherein the plane of each of the slit-imaged portion in the central region intersects said perpendicular plane at an angle substantially equal to arc tangent $\sqrt{2}$, arc tangent $\sqrt{2}$ being approximately equal to 55°.

7. A flow fluorometer according to claim 5, wherein each of said slit imaging systems comprises a slit field stop in an image plane of the respective optical system.

8. A flow fluorometer according to claim 7, wherein each of said slit field stops is angled with respect to said perpendicular plane at an angle substantially equal to arc tangent $\sqrt{2}$, arc tangent $\sqrt{2}$ being approximately equal to 55°.

9. A two-stage flow cytofluorometer for sequentially obtaining a one dimensional slit-scan type fluorescence contour of a biological cell and multi-dimensional slit-scan type fluorescence contours of the cell, comprising:
means for conveying the cell along a flow axis;
an illumination system including elements providing a substantially planar beam of electromagnetic radiation illuminating a planar region along said flow axis for exciting secondary fluorescence in the cell, the flow axis intersecting but not lying within the plane of the beam such that the cell passes through the beam and a plurality of substantially planar parallel cross-sections of the cell are successively excited to secondary fluorescence;

said illumination system further including elements providing a substantially cylindrical beam of electromagnetic radiation immediately downstream of the substantially planar beam for exciting secondary fluorescence in the cell, the cylindrical beam focus being such that a central region through which cells flow along the flow axis is illuminated;

a plurality of imaging systems each having an objective lens, each of said imaging systems including first optical axis elements for slit imaging through the respective objective lens across the central region, the first optical axes all lying substantially in a plane perpendicular to said flow axis and intersecting within the central region, the planes of the resultant slit-imaged portions in the central region being non-parallel with each other and non-parallel with said flow axis;

one of said imaging systems further including second optical axis elements for imaging the planar excited region through the respective objective lens, said second optical axis being angled with respect to the respective first optical axis so as to avoid interference therebetween;

a photodetector element coupled to said second optical axis elements for responding to secondary fluorescence from the successively excited cellular cross-sections as the cell passes through the substantially planar beam so as to generate a one-dimensional slit-scan type contour along an axis perpendicular to the substantially planar cellular cross-sections; and a photodetector element coupled to each of said first optical axis elements for responding to fluorescence from each of the slit-imaged portions in the central region, each of said photodetector means outputting a slit-scan type contour along a cellular axis perpendicular to the plane of the respective slit-imaged portion.

10. A two-stage flow cytofluorometer according to claim 9, which comprises three imaging systems having three respective sets of first optical axis elements defining three mutually orthogonal planar slit-imaged portions in the central region.

11. A flow cytofluorometer according to claim 10, wherein said first optical axes are angularly spaced at 120° within said perpendicular plane.

12. A two-stage flow cytofluorometer according to claim 10, wherein the plane of each of the slit-imaged portions in the central region intersects said perpendicular plane at an angle substantially equal to arc tangent $\sqrt{2}$, arc tangent $\sqrt{2}$ being approximately equal to 55°.

13. A two-stage flow cytofluorometer according to claim 10, wherein each of said slit imaging systems comprises a slit field stop in an image plane of the respective optical system.

14. A two-stage flow cytofluorometer according to claim 13, wherein each of said slit field stops is angled with respect to said perpendicular plane at an angle substantially equal to arc tangent $\sqrt{2}$, arc tangent $\sqrt{2}$ being approximately equal to 55°.

15. A two-stage flow cytofluorometer according to claim 12, wherein the substantially planar beam is perpendicular to said flow axis.

* * * * *